United States Patent [19]

Price et al.

[11] Patent Number: 4,703,989
[45] Date of Patent: Nov. 3, 1987

[54] ELECTRICAL CONNECTORS FOR A LIQUID SENSOR

[75] Inventors: James R. Price, Westminister; Kevin P. Leiner, Denver, both of Colo.

[73] Assignee: Cobe Laboratories, Inc., Lakewood, Colo.

[21] Appl. No.: 874,226

[22] Filed: Jun. 13, 1986

[51] Int. Cl.⁴ .......................................... H01R 13/625
[52] U.S. Cl. .................................... 439/283; 439/314; 439/344; 439/676; 439/932; 439/606
[58] Field of Search .................. 339/90 R, 90 C, 101, 339/102 R, DIG. 1, 176 M

[56] References Cited

U.S. PATENT DOCUMENTS

| | | | |
|---|---|---|---|
| 3,197,730 | 7/1965 | Hargett | 339/102 R |
| 3,239,125 | 3/1966 | Sherlock | 339/DIG. 1 |
| 3,252,124 | 5/1966 | Hansen | 339/90 R |
| 3,316,343 | 4/1967 | Sherlock | 339/DIG. 1 |
| 4,224,485 | 9/1980 | Krumreich | 339/176 M |
| 4,406,509 | 9/1983 | Jagen | 339/91 R |

Primary Examiner—John McQuade

[57] ABSTRACT

A two-piece electrical connection assembly comprising a first connector comprising a first insulating housing carrying plural first contacts in close proximity in a row, and a second mating connector for making connection between wires of a multiple conductor cable and said first contacts of said first connector, said second connector comprising a second insulating housing providing means for supporting second contacts aligned with said first contacts for mating with them and providing a spacing member, elongated second contacts having contact portions in position for mating with first contacts, connecting end portions connected to said wires, and spaced portions between said contact portions and said end portions and spaced from adjacent spaced portions by said spacing member, and heat shrunk plastic tubes surrounding the ends of said wires and said connecting end portions up to locations on said second contacts sufficiently close to said spacing member for the contacts to be spaced from each other, said tubes including melted solder sleeves therein electrically connecting said connecting end portions to said nonaligned wires.

6 Claims, 11 Drawing Figures

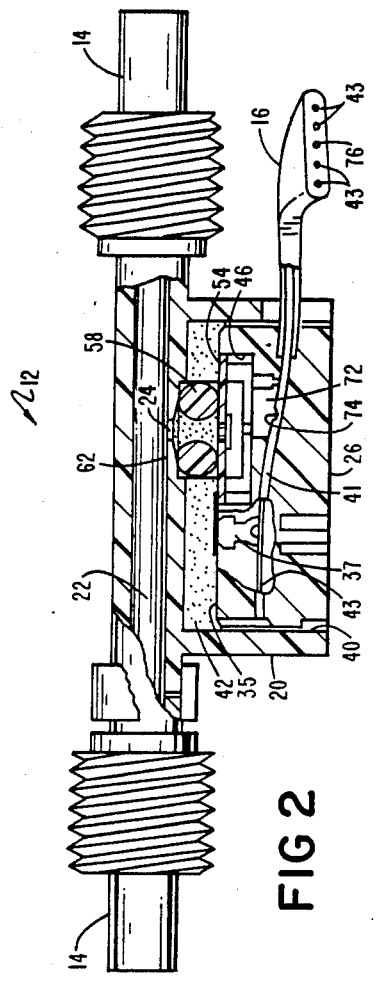
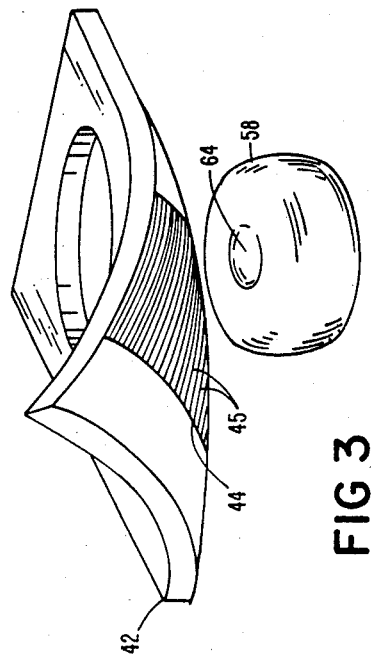
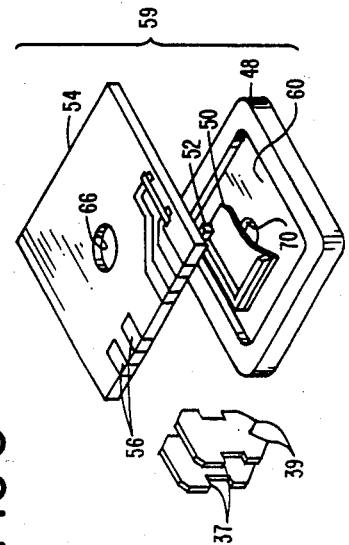
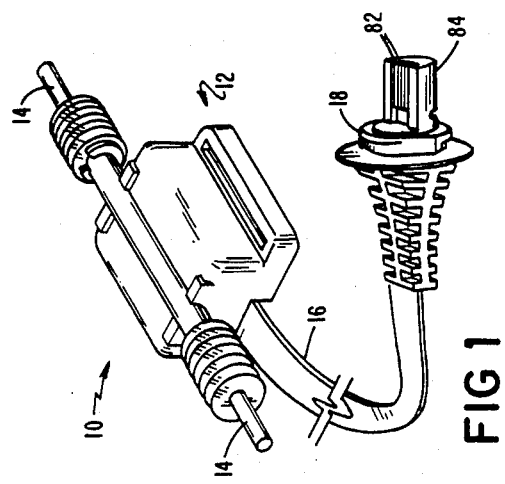
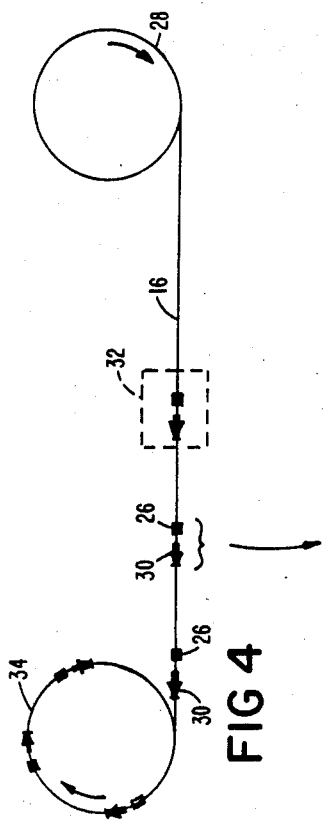

ELECTRICAL CONNECTORS FOR A LIQUID SENSOR

FIELD OF THE INVENTION

The invention relates to liquid sensors, e.g., disposable blood pressure transducers, connected by electrical wires to a monitor.

BACKGROUND OF THE INVENTION

A commercially available disposable blood pressure sensor includes a sensing element communicating through an opening in the side of a lumen which measures dynamic blood pressure in the cardiovascular system via a catheter and a tubing filled with isotonic fluid. The sensing element includes a strain gauge transducer (for example, the type having resistors ion-implanted in semiconductor material) in which a pressure change is sensed as a resistance change in a resistor bridge. A monitor, connected to the transducer by a wire permanently connected to the disposable unit and a reusable cable, supplies two terminals of the bridge with an excitation voltage, and detects an output signal at the other two terminals. The space between the lumen and the transducer is usually filled with a gel so as to transmit pressure without contact of the transducer with the blood, thereby providing electrical isolation of the patient from the sensing element.

SUMMARY OF THE INENTION

The invention features in general a two-piece connector assembly including a first connector with multiple contacts that are in close proximity in a row and a second connector for connecting the multiple contacts of the first connector to wires of a multiple conductor cable. The second connector has a housing that supports contacts that mate with the contacts of the first connector and are spaced from each other by a spacing member, and heat-shrunk plastic tubes surround the contacts and the ends of the wires and include melted solder sleeves within the tubes to electrically connect the wires to the contacts. The heat-shrunk plastic tubes permit connection of the closely spaced contacts to the wires without staggering the connections, permitting smaller overall size of the second connector.

In preferred embodiments, a rotatable locking ring is carried by the second connector and engages a protuberance on the first connector and provides a water-tight seal between the two; and the first connector contacts are insulation displacement blades having sharp ends piercing the insulation of the electrical wires.

The preferred use for the connector assembly is to make connections between a disposable blood pressure sensor and a monitor.

Other advantages and features of the invention will be apparent from the following description of a preferred embodiment thereof and from the claims.

DESCRIPTION OF THE PREFERRED EMBODIMENT

The drawings will be briefly described first.

DRAWINGS

FIG. 1 is a perspective view of a disposable blood pressure sensor according to the invention.

FIG. 2 is a partial elevation, partly in section, of the FIG. 1 sensor.

FIG. 3 is an exploded perspective view of a conductor-carrying elastomeric sheet, an elastomeric displacement sealing ring and a sensing element of the FIG. 1 sensor.

FIG. 4 is a schematic of the manufacturing process for the molded end peices of the FIG. 1 sensor.

FIG. 4a is an elevation of part of the wire carrying a pair of nearby plastic end pieces during the manufacturing process shown in FIG. 4.

STRUCTURE

Figure 5:
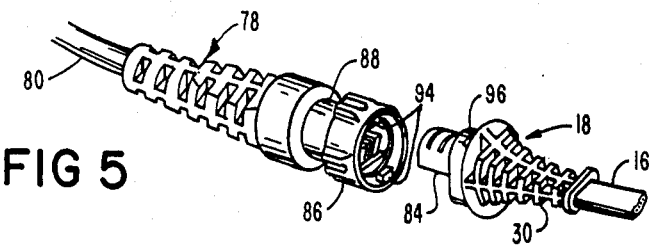
FIG. 5 is a perspective view showing a two-piece connection assembly including an electrical connector of the FIG. 1 sensor and a connector of a reusable cable attached to a monitor.

Referring to FIG. 1, there is shown disposable blood sensor 10 including sensing unit 12 with threaded ends 14 for connection to a fluid filled tube connected to the cardiovascular system via a catheter via linden nuts (all three not shown), and pigtail multiconductor electrical wire 16 and electrical connector 18.

Referring to FIG. 2, it is seen that sensing unit 12 includes clear plastic housing 20 defining fluid path 22 having opening 24 between it and cavity 40 inside of the lower portion of clear plastic housing 20. Plastic molded end piece 26 is mounted in cavity 40. End piece 26 is molded around the end of wire 16 by the process shown in FIG. 4. Wire 16 is unwound from supply reel 28, and connecting end piece 26 and plastic housing 30 of connector 18 are simultaneously molded around nearby portions of wire 16 at molder 32 prior to rewinding on take-up reel 34. Wire 16 is advanced by slightly more than the desired length between end piece 26 and housing 30 between each molding step. In a further manufacturing step, the individual pieces of wire 16 with connecting end piece 26 and housing 30 on respective ends are provided by slicing wire 16 at the small pieces 36 of wire 16 between nearby pairs of end pieces 26 and housings 30, removing pieces 36 and sealing off exposed conductors.

Referring to FIGS. 2 and 3 four insulation displacement blades 37 are inserted in molded channels in the upper surface of end piece 26. Blades 37 have sharp pointed ends 39 that pierce insulation 41 covering conductors 43 making electrical contact with them. Blades 37 are made of 0.014" thick phosphor bronze, spring tempered, and provided with hard gold plate over nickel. Manufactured in continuous strips, they are easily automatically handled by an insertion machine.

Sandwiched between upper surface 35 of molded end piece 26 and the lower surface 38 at the top of cavity 40 of housing 20 is elastomeric sheet 42 carrying metalization 44 on its lower surface. Provided in upward-facing recess 46 of end piece 26 are lid 48, semiconductor strain gauge transducer 50, adhesive sealing ring 52 around the periphery of transducer 50 and above it, ceramic substrate 54 carrying conductive paths 56, and elastomeric displacement sealing O-ring 58. Displacement sealing ring 58 is sufficiently compressed so as to reduce its interior volume by an amount to cause displacement of gel so as to occupy all space between it and opening 24, as is discussed below. Metallization 44 may include for example a plurality of fine separate parallel lines 45 extending longitudinally on sheet 42 for making electrical contact between blades 37 and respective conductive paths 56. Sheet 42 is made of material such as silicone, and metal lines 45, in the preferred embodiment, are each 5 mils wide and spaced from adjacent lines by 5 mils and are made of copper coated with nickel and gold. On the lower surface of semiconductive transducer 50 is a layer of isolation gel (not shown) within recess 60 of lid 48.

In manufacture, semiconductor transducer 50 is adhered to the bottom of ceramic substrate 54 by adhesive 52; electrical wires (not shown) are added to electrically connect transducer 50 to substrate 54; the isolation gel is applied to the lower surface of transducer 50, and lid 48 is adhered to the lower surface of ceramic substrate 54. The assembled unit including lid 48, transducer 50 and substrate 54 are collectively referred to herein as sensing element 59, as indicated on FIG. 3. Displacement sealing ring 58 is adhesively adhered to the upper surface of the ceramic substrate 54, and isolation gel 62 is injected into opening 64 of ring 58 and passes down through hole 66 of substrate 54 and into the region between the lower surface of substrate 54 and the upper surface of transducer 50, filling all voids within sensing element 59 and ring 58. Sensing element 59 and attached ring 58 are placed in recess 46 of end piece 26, which is inserted in cavity 40 of housing 20 with elastomeric sheet 42 between surface 38 of housing 20 and facing surface 35. Prior to staking end piece 26 to housing 20, displacement sealing ring 58 is compressed, causing gel 62 therein to rise upward into opening 24. Elastomeric sheet 42 is similarly compressed prior to staking, providing a liquid tight seal between surface 38 surrounding opening 24 and upper surface 35 of plastic end piece 26. Sealing ring 58 similarly provides a liquid tight seal between opening 24 and the exposed upper surface of sensing element 59, providing a communication path between the two for communicating pressure. Lid 48 includes venting hole 70 which communicates with channel 72 in the center bottom of recess 46, in turn communicating with hole 74 provided to the center channel 76 of wire 16 from which the conductor has been removed to provide venting to the space within recess 60 of lid 48.

Figure 6:
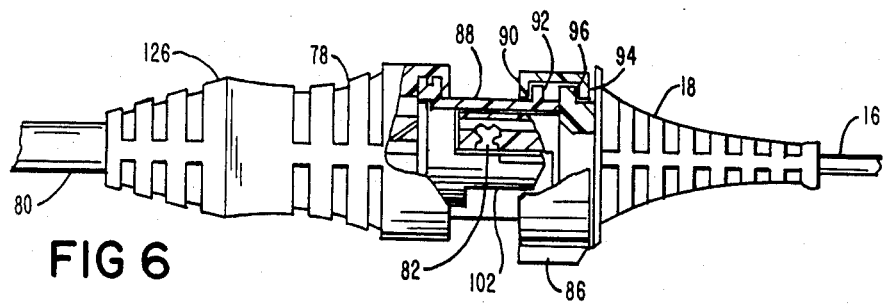
FIG. 6 is an elevation, partially broken away, showing the FIG. 5 connectors connected together.

Referring to FIGS. 5-6, connector 18 of disposable blood sensor 10 is shown in position for mating with connector 78 of reusable cable 80, connected to a monitor (not shown). Connector 18 includes four insulation displacement blades 82 in insertion end 84 (FIGS. 1, 6). Blades 82 have sharp pointed ends piercing the insulation of wire 16 and making electrical connection with respective conductors 43 in housing 30. Connector 78 includes locking and sealing ring 86 that is rotatably mounted on end tube 88 and retained by lip 90 on ring 86 and tabs 92 on end tube 88. Ring 86 includes two tabs 94 that mate with camming surfaces 96 of connector 18.

Figure 7:
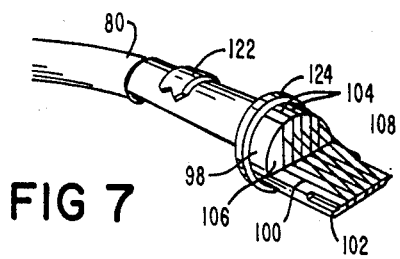
FIG. 7 is a perspective view of a component of the FIG. 5 connector attached to the reusable cable prior to final assembly.
Figure 8:
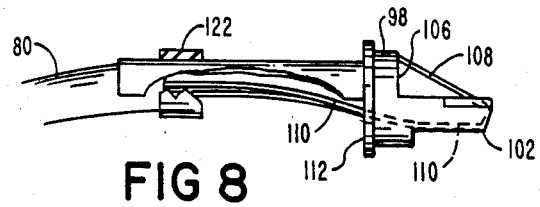
FIG. 8 is a side elevation, partially broken away, of the FIG. 7 component.
Figure 9:
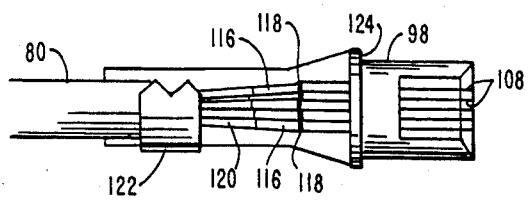
FIG. 9 is a bottom plan view of the FIG. 7 component.
Figure 10:
FIG. 10 is a elevation showing a heat shrinkable tube and inserted contact and wire of the FIG. 7 component prior to heat shrinking.

Referring to FIGS. 7-9, it is seen that inside of end tube 88 is plastic contact support 98 including grooves 100 in the flat surface of extension 102 and grooves 104 in the face of surface 106 perpendicular to the flat surface of extension 102. Resilient contact members 108 (gold plated phosphor bronze wires, about 18 mils in diameter for example) extend from grooves 100 at the end of extension 102 to grooves 104, and have free ends in grooves 104, permitting resilient pivoting about the end of extension 102. Referring to FIGS. 8 and 9, it is seen that midsections 110 of contacts 108 pass through spaced channels in base 112 of support 98 in which they are retained. Referring to FIGS. 9 and 10, connection ends 114 of contacts 108 are within heat shrunk plastic tubes 116 having solder sleeves 118 therein. Tubes 116 extend up to base 112, where midsections 110 of the contacts are spaced from each other, owing to mounting in separate channels of base 112. Ends 114 are connected to electrical wires 120, the ends of which are also in heat shrunk tubes 116. As can best be seen in FIG. 9, contacts 108 are aligned in close proximity with each other and are connected to a plurality of non-aligned overlapping wires 120 in cable 80. Heat shrunk tubes 116 permit the connection between the two without the use of staggering of connections, contributing to the small overall size of connector 78. In manufacture, after the contacts have been mounted in support 98 and connected to wires 120, clip 122 is provided, as shown in FIGS. 7-9; end tube 88, carrying locking ring 86, is then slid over extension 102 and up against lip 124, and outside plastic cover 126 is molded around the entire assembly.

OPERATION

In use, ends 14 of disposable sensor 10 are secured to an isotonic fluid filled tube using linden nuts. Pressure signals from the patient's vascular system communicate its pressure to gel 62 in opening 24, which in turn communicates it to the upper surface of semiconductor strain gauge 50, and the pressure is determined by electrical signals received by the monitor (not shown). Electrical connection from ceramic substrate 54 to wire 16 is provided by the parallel conductor lines 45 on the bottom of elastomer sheet 42, and insulation displacement blades 37.

Locking ring 86 provides a liquid resistant seal and positive locking between connectors 18, 78. Elastomer sheet 42 provides a liquid tight seal within sensing unit 12.

OTHER EMBODIMENTS

Other embodiments of the invention are within the scope of the following claims. For example, instead of a large number of thin metal lines 45, four discrete conductors, aligned with blades 37 and conductive paths 56, could be used to provide electrical connection between the two.

What is claimed is:

1. A two-piece electrical connection assembly for connecting a disposable blood sensor to a monitor, said assembly comprising
    a disposable blood sensor connected to one end of an electrical wire having multiple conductors in insulation,
    a disposable first connector comprising an insulating body molded around the other end of said electrical wire and carrying plural first contacts in parallel arrangement in said body in close proximity in a row,
    said first contacts comprising insulation displacement blades having sharp ends piercing said insulation and contacting said conductors, and a reusable second mating connector for making connection between wires of a multiple conductor cable and said first contacts of said first connector, said second connector comprising an insulating housing providing means for supporting second contacts aligned with said first contacts for mating with them and providing a spacing member, elongated second contacts having contact portions in position for mating with first contacts, connecting end portions connected to said wires, and spaced portions between said contact portions and said end portions and spaced from adjacent spaced portions by said spacing member, and heat shrunk plastic tubes surrounding the ends of said wires and said connecting end portions up to locations on said second contacts sufficiently close to said spacing member for the contacts to be spaced from each other, said tubes including melted solder therein electrically connecting said connecting end portions to said wires, said housing including a jacket molded around said means for supporting second contacts and said tubes and said cable, said body and said housing of said first and second connectors including integral means for providing a liquid resistant connection between the two.

2. The assembly of claim 1 wherein said insulating housing defines grooves receiving said contact portions, and said contact portions are movable.

3. The assembly of claim 1 wherein said integral means for providing a liquid resistant connection comprises a radial protuberance on said first connector and a rotatable locking ring carried by said insulating housing for lockably engaging said protuberance.

4. The assembly of claim 3 wherein said protuberance has a camming surface.

5. The assembly of claim 3 wherein said locking ring is carried by an end tube surrounding said contact portions.

6. The assembly of claim 2 wherein there are two transverse surfaces having grooves receiving said contact portions.

* * * * *